(12) United States Patent
Pearlman et al.

(10) Patent No.: US 9,663,801 B2
(45) Date of Patent: *May 30, 2017

(54) METHODS OF PRODUCING FOUR CARBON MOLECULES

(75) Inventors: Paul S. Pearlman, Thornton, PA (US); Changlin Chen, Ingleby Barwick (GB); Adriana L. Botes, Rosedale East (GB)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/524,973

(22) Filed: Jun. 15, 2012

(65) Prior Publication Data

US 2013/0210104 A1 Aug. 15, 2013

Related U.S. Application Data

(60) Provisional application No. 61/498,408, filed on Jun. 17, 2011.

(51) Int. Cl.
| | | |
|---|---|---|
| *C12P 5/02* | (2006.01) | |
| *C12P 7/16* | (2006.01) | |
| *C12P 7/18* | (2006.01) | |
| *C12N 9/02* | (2006.01) | |
| *C12N 9/88* | (2006.01) | |
| *C12N 15/52* | (2006.01) | |

(52) U.S. Cl.
CPC .............. *C12P 5/026* (2013.01); *C12N 9/001* (2013.01); *C12N 9/0071* (2013.01); *C12N 9/88* (2013.01); *C12N 15/52* (2013.01); *C12P 5/02* (2013.01); *C12P 7/16* (2013.01); *C12P 7/18* (2013.01); *C12Y 103/01035* (2013.01); *C12Y 103/08* (2013.01); *C12Y 114/11022* (2013.01); *C12Y 401/01033* (2013.01); *C12Y 402/01* (2013.01); *C12Y 402/01127* (2013.01); *C12Y 402/03027* (2013.01); *Y02E 50/10* (2013.01); *Y02E 50/343* (2013.01); *Y02P 20/52* (2015.11)

(58) Field of Classification Search
None
See application file for complete search history.

(56) References Cited

U.S. PATENT DOCUMENTS

| 8,703,455 | B2 | 4/2014 | Marliere |
|---|---|---|---|
| 8,741,612 | B2 | 6/2014 | Campbell et al. |
| 2011/0165644 | A1 | 7/2011 | Marliere |
| 2011/0300597 | A1 | 12/2011 | Burk et al. |
| 2012/0021478 | A1 | 1/2012 | Osterhout et al. |
| 2012/0122563 | A1 | 5/2012 | Walker et al. |
| 2012/0225466 | A1 | 9/2012 | Burk et al. |
| 2013/0189753 | A1 | 7/2013 | Pearlman et al. |
| 2013/0309742 | A1 | 11/2013 | Campbell et al. |
| 2014/0065686 | A1 | 3/2014 | Marliere |
| 2014/0141482 | A1 | 5/2014 | Pearlman et al. |
| 2014/0186913 | A1 | 7/2014 | Botes et al. |
| 2015/0037860 | A1 | 2/2015 | Botes et al. |
| 2015/0079654 | A1 | 3/2015 | Botes et al. |

FOREIGN PATENT DOCUMENTS

| EP | 2336340 A1 | 6/2011 |
|---|---|---|
| EP | 2336341 A1 | 6/2011 |
| WO | WO2009155382 A1 | 12/2009 |
| WO | WO2010001078 | 1/2010 |
| WO | WO2010099201 A1 | 9/2010 |
| WO | WO 2011/011689 | 1/2011 |
| WO | WO 2011/076261 | 6/2011 |
| WO | WO 2011/076689 | 6/2011 |
| WO | WO 2011/076691 | 6/2011 |
| WO | WO 2011/079314 | 6/2011 |
| WO | WO2011140171 A2 | 11/2011 |
| WO | WO2012018624 A2 | 2/2012 |
| WO | WO 2012/052427 | 4/2012 |
| WO | WO2012174439 A2 | 12/2012 |
| WO | WO 2013/007786 | 1/2013 |
| WO | WO 2013/020118 | 2/2013 |
| WO | WO 2013/028519 | 2/2013 |
| WO | WO 2013/040383 | 3/2013 |
| WO | WO2013036812 | 3/2013 |
| WO | WO 2013/057194 | 4/2013 |
| WO | WO 2013/090915 | 6/2013 |
| WO | WO 2013/092567 | 6/2013 |
| WO | WO2013082542 A2 | 6/2013 |
| WO | WO 2013/150100 | 10/2013 |
| WO | WO 2013/173437 | 11/2013 |
| WO | WO 2013/181647 | 12/2013 |
| WO | WO 2013/192183 | 12/2013 |
| WO | WO2013188546 | 12/2013 |
| WO | WO 2014/001517 | 1/2014 |
| WO | WO 2014/033129 | 3/2014 |
| WO | WO 2014/064198 | 5/2014 |

(Continued)

OTHER PUBLICATIONS

Kizer L et al. Application of Functional Genomics to Pathway Optimization for Increased Isoprenoid Production. 2008. Applied and Environmental Microbiology. vol. 74, No. 10. p. 3229-3241.*
Prather K et al. De novo biosynthetic pathways: rational design of microbial chemical factories. 2008, 19: 468-474.*
Daniel R et al. Biochemistry of coenzyme B12-dependent glycerol and diol dehydratases and organization of the encoding genes. 1999. FEMS Microbiology Reviews. 22:553-566.*
Kelada SN et al. Delta-aminolevulinic acid dehydratase genotype and lead toxicity: A HuGE Review. 2001. American Journal of Epidemiology. 154(1). 1-13.*
Toraya T. Radical catalysis of B12 enzymes: structure, mechanism, inactivation, and reactivation of diol and glycerol dehydratases. 2000. Cellular and Molecular Life Sciences. 57:106-127.*
Rettie et al., "CYP4 Isozyme Specificity and the Relationship between w-Hydroxylation and Terminal Desaturation of Valproic Acid," Biochemistry, 34, 7889-7895 (1995).

(Continued)

*Primary Examiner* — Paul Holland
(74) *Attorney, Agent, or Firm* — Licata & Tyrrell P.C.

(57) ABSTRACT

Disclosed are methods for producing butadiene from one or more of several diverse feedstocks including bioderived feedstocks, renewable feedstocks, petrochemical feedstocks and natural gas.

12 Claims, 5 Drawing Sheets

(56) References Cited

FOREIGN PATENT DOCUMENTS

| | | |
|---|---|---|
| WO | WO 2014/085612 | 6/2014 |
| WO | WO 2014/015210 | 11/2014 |

OTHER PUBLICATIONS

Wang et al., "Alteration of Product Specificity of Rhodobacter sphaeroides Phytoene Desaturase by Direct Evolution," J. Biolog. Chem., vol. 27, No. 44, Issue of Nov. 2, pp. 41161-41164 (2001).
Barta et al., "Structural basis for nucleotide binding and reaction catalysis in mevalonate diphosphate decarboxylase," Biochemistry, 51(28):5611-5621, Epub Jul. 6, 2012.
Becker et al., "Metabolic flux engineering of L-lysine production in Corynebacterium glutamicum—over expression and modification of G6P dehydrogenase," Journal of Biotechnology, 132(2):99-109, Epub Jun. 6, 2007.
Brigham et al., "Engineering Ralstonia eutropha for Production of Isobutanol from CO2, H2, and O2," Advanced Biofuels and Bioproducts, Chapter 39, 1065-1090, 2012.
Brodkorb et al., "Linalool dehydratase-isomerase, a bifunctional enzyme in the anaerobic degradation of monoterpenes," J Biol Chem., 285(40):30436-30442, Epub Jul. 27, 2010.
Buckel et al., "Glutaconate CoA-transferase from Acidaminococcus fermentans," Eur J Biochem., 118(2):315-321, Aug. 1981.
Bugg et al., "The emerging role for bacteria in lignin degradation and bio-product formation," Curr Opin Biotechnol., 22 (3):394-400, Epub Nov. 9, 2010.
Chayabutra and Ju, ""Degradation of n-hexadecane and its metabolites by Pseudomonas aeruginosa under microaerobic and anaerobic denitrifying conditions,""Appl Environ Microbiol., 66(2):493-498, Feb. 2000.
Chung and Rhee, "Overexpression of the (R)-specific enoyl-CoA hydratase gene from Pseudomonas chlororaphis HS21 in Pseudomonas strains for the biosynthesis of polyhydroxyalkanoates of altered monomer composition," Biosci. Biotechnol. Biochem., 76(3): 613-616, 2012.
Dhe-Paganon et al., "Mechanism of mevalonate pyrophosphate decarboxylase: evidence for a carbocationic transition state," Biochemistry, 33(45):13355-13362, Nov. 15, 1994.
Eikmanns and Buckel, "Crystalline green 5-hydroxyvaleryl-CoA dehydratase from Clostridium aminovalericum," Eur. J. Biochem., 197(3):661-668, May 8, 1991.
Ferrandez et al., "Genetic characterization and expression in heterologous hosts of the 3-(3-hydroxyphenyl)propionate catabolic pathway of Escherichia coli K-12," J. Bacteriol., 179(8): 2573-2581, Apr. 1997.
Gogerty and Bobik, "Formation of isobutene from 3-hydroxy-3-methylbutyrate by diphosphomevalonate decarboxylase," Appl Environ Microbiol., 76(24):8004-8010, Epub Oct. 22, 2010.
Guan et al., "Cytochrome P450-dependent desaturation of lauric acid: isoform selectivity and mechanism of formation of 11-dodecenoic acid," Chem Biol Interact., 110(1-2):103-121, Mar. 1998.
He and Spain, "A novel 2-aminomuconate deaminase in the nitrobenzene degradation pathway of Pseudomonas pseudoalcaligenes JS45," J Bacteriol., 180(9):2502-2506, May 1998.
Hermann et al, "Industrial production of amino acids by coryneform bacteria," J Biotechnol., 104(1-3):155-172, Sep. 2003.
Jang et al., "Bio-based production of C2-C6 platform chemicals," Biotechnol Bioeng., 109(10):2437-2459, Epub Jul. 13, 2012.
Jaremko and Yu, "The initial metabolic conversion of levulinic acid in Cupriavidus necator," J Biotechnol., 155 (3):293-298, Epub Jul 30, 2011.
Kasai et al., "Uncovering the protocatechuate 2,3-cleavage pathway genes," J Bacteriol., 191(21):6758-6768, Epub Aug. 28, 2009.
Kim et al., "An allylic ketyl radical intermediate in clostridial amino-acid fermentation," Nature., 452(7184):239-242, Mar. 2008.
Kim, "On the enzymatic mechanism of 2-hydroxyisocaproyl-CoA dehydratase from Clostridium difficile," 2004, Ph.D. dissertation, Philipps-Universität, Marburg, 2004.
Köpke et al., "2,3-butanediol production by acetogenic bacteria, an alternative route to chemical synthesis, using industrial waste gas," Appl Environ Microbiol., 77(15):5467-5475, Epub Jun. 17, 2011.
Kuzma et al., "Bacteria produce the volatile hydrocarbon isoprene," Curr Microbiol., 30(2):97-103, Feb. 1995.
Kuzuyama, "Mevalonate and nonmevalonate pathways for the biosynthesis of isoprene units," Biosci Biotechnol Biochem., 66(8):1619-1627, Aug. 2002.
Lee et al., "Synthesis of pure meso-2,3-butanediol from crude glycerol using an engineered metabolic pathway in Escherichia coli," Appl Biochem Biotechnol., 166(7):1801-1813, Epub Mar. 21, 2012.
Li et al., "Cupriavidus necator JMP134 rapidly reduces furfural with a Zn-dependent alcohol dehydrogenase," Biodegradation, 22(6): 1215-1225, Nov. 2011.
Lim et al., "Amplification of the NADPH-related genes zwf and gnd for the oddball biosynthesis of PHB in an E. coli transformant harboring a cloned phbCAB operon," J Biosci Bioeng., 93(6):543-549, 2002.
Liu et al., "Microbial production of R-3-hydroxybutyric acid by recombinant E. coli harboring genes of phbA, phbB, and tesB," Appl Microbiol Biotechnol., 76(4):811-818, Epub Jul. 4, 2007.
Luo et al., "Production of 3-hydroxypropionic acid through propionaldehyde dehydrogenase PduP mediated biosynthetic pathway in Klebsiella pneumoniae," Bioresour Technol., 103(1):1-6, Epub Oct. 2, 2011.
Martin and Prather, "High-titer production of monomeric hydroxyvalerates from levulinic acid in Pseudomonas putida," J Biotechnol., 139(1):61-67, Epub Sep. 25, 2008.
Meijnen et al., "Improved p-hydroxybenzoate production by engineered Pseudomonas putida S12 by using a mixed-substrate feeding strategy," Appl Microbiol Biotechnol., 90(3):885-893, Epub Feb. 2, 2011.
Mo et al., "Biosynthesis of the allylmalonyl-CoA extender unit for the FK506 polyketide synthase proceeds through a dedicated polyketide synthase and facilitates the mutasynthesis of analogues," J Am Chem Soc., 133(4):976-985, Epub Dec. 22, 2010.
Muraki et al., "Prokaryotic homologs of the eukaryotic 3-hydroxyanthranilate 3,4-dioxygenase and 2-amino-3-carboxymuconate-6-semialdehyde decarboxylase in the 2-nitrobenzoate degradation pathway of Pseudomonas fluorescens strain KU-7," Appl Environ Microbiol., 69(3):1564-1572, Mar. 2003.
Ohashi et al., "Continuous production of lactic acid from molasses by perfusion culture of Lactococcus lactis using a stirred ceramic membrane reactor," J Biosci Bioeng., 87(5):647-654, 1999.
Papanikolaou et al., "Citric acid production by Yarrowia lipolytica cultivated on olive-mill wastewater-based media," Bioresour Technol., 99(7):2419-2428, Epub Jul. 2, 2007.
Pérez-Pantoja et al., "Metabolic reconstruction of aromatic compounds degradation from the genome of the amazing pollutant-degrading bacterium Cupriavidus necator JMP134," FEMS Microbiol Rev., 32(5):736-794, Epub Aug. 7, 2008.
Przybylski et al., "Third-generation feed stocks for the clean and sustainable biotechnological production of bulk chemicals: synthesis of 2-hydroxyisobutyric acid," Energy, Sustainability and Society, 2:11, 2012.
Ramsay et al., "Use of a nylon manufacturing waste as an industrial fermentation substrate," Appl Environ Microbiol., 52(1):152-156, Jul. 1986.
Schäfer et al., "Synthesis of short-chain diols and unsaturated alcohols from secondary alcohol substrates by the Rieske nonheme mononuclear iron oxygenase MdpJ.," Appl Environ Microbiol., 78(17):6280-6284, Epub Jun. 29, 2012.
Scherf and Buckel, "Purification and properties of an iron-sulfur and FAD-containing 4-hydroxybutyryl-CoA dehydratase/vinylacetyl-CoA delta 3-delta 2-isomerase from Clostridium aminobutyricum," Eur J Biochem., 215 (2):421-429, Jul. 15, 1993.
Scherf et al., "Succinate-ethanol fermentation in Clostridium kluyveri: purification and characterisation of 4-hydroxybutyryl-

(56) References Cited

OTHER PUBLICATIONS

CoA dehydratase/vinylacetyl-CoA delta 3-delta 2-isomerase," Arch Microbiol., 161(3):239-245, 1994.
Seedort et al., "The genome of *Clostridium kluyveri*, a strict anaerobe with unique metabolic features," Proc Natl Acad Sci U S A., 105(6):2128-2133, Epub Jan. 24, 2008.
Shen et al., "Driving forces enable high-titer anaerobic 1-butanol synthesis in *Escherichia coli*," Appl Environ Microbiol., 77(9):2905-2915, Epub Mar. 11, 2011.
Silver and Fall, "Characterization of aspen isoprene synthase, an enzyme responsible for leaf isoprene emission to the atmosphere," J Biol Chem., 270(22):13010-13016, Jun. 2, 1995.
Sweeney et al., "Physiologically based pharmacokinetic modeling of 1,3-butadiene, 1,2-epoxy-3-butene, and 1,2:3,4-diepoxybutane toxicokinetics in mice and rats," Carcinogenesis., 18(4):611-625, Apr. 1997.
Tseng et al., "Biosynthesis of chiral 3-hydroxyvalerate from single propionate-unrelated carbon sources in metabolically engineered *E. coli*," Microb Cell Fact., 9:96, Nov. 27, 2010.
Tsuge et al., "Molecular characterization and properties of (R)-specific enoyl-CoA hydratases from Pseudomonas aeruginosa: metabolic tools for synthesis of polyhydroxyalkanoates via fatty acid beta-oxidation," Int J Biol Macromol., 31(4-5):195-205, Jan. 2003.
Ulmer et al., "Bacterial production of poly(.beta.-hydroxyalkanoates) containing unsaturated repeating units by Rhodospirillum rubrum," Macromolecules, 27(7):1675-1679, 1994.
Upton and Mckinney, "Role of the methylcitrate cycle in propionate metabolism and detoxification in *Mycobacterium smegmatis*," Microbiology, 153(Pt 12):3973-3982, Dec. 2007.
van Leeuwen et al., "Fermentative production of isobutene," Appl Microbiol Biotechnol., 93(4):1377-1387, Epub Jan. 11, 2012.
Wee et al., "Biotechnological production of lactic acid and its recent applications," Food Technol. Biotechnol., 44(2): 163-172, 2006.
Wendt et al., "Crystal structure of the carboxyltransferase subunit of the bacterial sodium ion pump glutaconyl-coenzyme A decarboxylase," EMBO J., 22(14):3493-3502, Jul. 15, 2003.
White, "Butadiene production process overview," Chem Biol Interact., 166(1-3):10-14, Epub Jan. 26, 2007.
Yang et al., "Value-added uses for crude glycerol—a byproduct of biodiesel production," Biotechnology for Biofuels, 5:13, Mar. 14, 2012.
Uniprot Accession No. P32377, Jun. 15, 2010, 4 pages.
Uniprot Accession No. Q7CCL9, Jun. 15, 2010, 2 pages.
Uniprot Accession No. B8ZLF3, Jun. 15, 2010, 2 pages.
International Preliminary Report on Patentability and Written Opinion for PCT/US2012/042757, issued Dec. 17, 2013, 7 pages.
International Search Report in Application No. PCT/US2012/042757 mailed Mar 6, 2013, 5 pages.
International Search Report in Application No. PCT/US2012/067463, mailed Jun. 17, 2013, 19 pages.
Invitation to pay additional fees and, where applicable, protest fee for PCT/US2012/067463, mailed Mar. 13, 2013, 17 pages.
Buckel et al., "2-Hydroxyacyl-CoA dehydratases, a novel family of molybdenum enzymes," J Inorganic Biochemistry, 2003, 96(1):53, 1 page.
European Communication Pursuant to Rules 161(1) and 162 EPC in application No. EP 12799032.3, mailed Jul. 18, 2014, 10 pages.
Forster-Fromme et al., "Biochemical characterization of isovaleryl-CoA dehydrogenase (LiuA) of Pseudomonas aeruginosa and the importance of liu genes for a functional catabolic pathway of methyl-branched compounds," FEMS Microbiol Lett, 2008, 286(1):78-84.
Genbank accession No. AAD44196.1, Oct. 15, 1999, 1 page.
Genbank accession No. AAG05403.1, Jan. 31, 2014, 2 pages.
Genbank accession No. AAV40818.1, Feb. 4, 2005, 1 page.
Genbank accession No. AAV40819.1, Feb. 4, 2005, 1 page.
Genbank accession No. AAV40820.1, Feb. 4, 2005, 1 page.
Genbank accession No. BAA21816.1, Aug. 19, 1997, 2 pages.
Genbank accession No. BAA92740, Aug. 1, 2007, 2 pages.
Genbank accession No. CAA32465.1, Jul. 26, 1995, 1 page.
Genbank accession No. CAA32466.1, Jul. 26, 1995, 1 page.
Genbank accession No. CAA42196.1, Oct. 16, 1995, 1 page.
Genbank accession No. CAA99573.1, Nov. 14, 2006, 2 pages.
Genbank accession No. NP_746661, Jun. 27, 2013, 2 pages.
International Preliminary Report on Patentability and Written Opinion for PCT/US2012/064407, issued May 13, 2014, 8 pages.
International Preliminary Report on Patentability and Written Opinion for PCT/US2012/067463, issued Jun. 3, 2014, 12 pages.
International Search Report and Written Opinion in Application No. PCT/US2013/072275, mailed Mar. 6, 2014, 12 pages.
International Search Report and Written Opinion in Application No. PCT/US2013/045430, mailed Feb. 3, 2014, 20 pages.
International Search Report in Application No. PCT/US2012/064407, mailed Feb. 7, 2013, 13 pages.
Invitation to pay additional fees and, where applicable, protest fee for PCT/US2013/045430, mailed Nov. 25, 2013, 6 pages.
Kim et al., "Dehydration of ®-2-hydro9xyacyl-CoA to enoyl-CoA in the fermentation of α-amino acids by anaerobic bacteria," FEMS Microbiol Rev, 2004, 28(4):455-468, 14 pages.
Lan et al., "ATP drives direct photosynthetic production of 1-butanol in cyanobacterial," PNAS, 2012, 109(16):6018-6023, 6 pages.
Lee et al., "Conversion of beta-methylbutyric acid to beta-hydroxy-beta-methylbutyric acid by Galactomyces reessii," Appl Environ Microbiol, 1997, 63(11):4191-4195, 5 pages.
Li et al., "JMP134 rapidly reduces furfural with a Zn-dependent alcohol dehydrogenase," Biodegradation, 2011, 22(6):1215-1225, 11 pages.
Martin et al., "Engineering a Mevalonate pathway to *Escherichia coli* for production of terpenoids," Nature Biothechnology, 2003, 21:796-802.
Morone et al., "Increasing diterpene yield with a modular metabolic engineering system in *E. coli*: comparison of MEV and MEP isoprenoid precursor pathway engineering," Applied Microbiology and Biotechnology, 2010, 85:1893-1906.
U.S. Non-Final Office Action in U.S. Appl. No. 13/691,623, mailed Jun. 25, 2014, 13 pages.
Yang et al., "Enhancing production of bio-isoprene using hybrid MVA pathway and isoprene synthase in *E. coli*," PLoS One, Apr. 2012, 7:1-7.
Zhao et al., "Biosynthesis of isoprene in *Escherichia coli* via methylerythritol phosphate (MEP) pathway," *Applied Microbilogy and Biotechnology*, Apr. 2011, 90:1915-1922.
Fukui et al., "Expression and characterization of (R)-specific enoyl coenzyme A hydratase involved in polyhydroxyalkanoate biosynthesis by Aeromonas caviae," J. Bacteriology, Feb. 1998, 180(3):667-673.
Gehret et al., "Terminal alkene formation by the thioesterase of curacin A biosynthesis: structure of a decarboxylating thioesterase," J. Of Biological Chem., 2011, 186(16):14445-14454.
Genbank accession No. E1XUJ2.1. Sep. 5, 2012, 2 pages.
Gu et al., "Polyketide Decarboxylative chain Termination Preceded by *O*-sulfonation in curacin A Biosynthesis," J. Am. Chemical Soc., Nov. 2009, 131(44):16033-16035.
International Preliminary Report on Patentability in International Application No. PCT/US2013/045430, mailed Dec. 24, 2014, 12 pages.
International Search Report and Written Opinion in Application No. PCT/US2014/048606, mailed Oct. 31, 2014, 19 pages.
International Search Report and Written Opinion in Application No. PCT/US2014/049807, mailed Nov. 5, 2014, 56 pages.
Jin et al., "The selective addition of water to C=C bonds; enzymes are the best chemists," Chem Commun., 2011, 47:2502-2510.
Luddeke et al. "Geraniol and Geranial Dehydrogenases Induced in Anaerobic Monoterpene Degradation by Castellaniella defragrans," Appl. And Environmental Microbiology, 2012, 78(7): 2128-2136.
Luddeke et al., "Enantiospecific (S)-(+)-linalool formation from beta-myrcene by linalool dehydratase-isomerase," Z Naturforsch C., Jul./Aug. 2011, 66(7-8):409-412.
McCarthy et al., "Structural basis of functional group activation by sulfotransferases in complex metabolic pathways," ACS Chem. Biol., 2012, 7:1994-2003.

(56) References Cited

OTHER PUBLICATIONS

Rude et al., "Terminal olefin (1-alkene) biosynthesis by a novel p450 fatty acid decarboxylase from *Jeotgalicoccus* speciesm," Appl. Environ. Microbiol., 2011, 77(5):1718-1727.
Uniprot Accession No. I3RA72, Sep. 5, 2012, 2 pages.
US Final Office Action in U.S. Appl. No. 13/691,623, mailed Dec. 9, 2014, 15 pages.
US Non-Final Office Action in U.S. Appl. No. 13/092,115, mailed Apr. 1, 2015, 21 pages.
Akatsuka et al., "The Serratia marcescens bioH gene encodes an esterase," GENE, Jan. 2003, 302:185-192.
Eriksen et al., "Protein Design for Pathway Engenieering," Journal of Structural Biology, Apr. 2013, 185(2):234-242.
Invitation to pay additional fees and, where applicable, protest fee for PCT/US2015/036095, mailed Sep. 18, 2015, 13 pages.
Lin et al., "The BioC O-Methyltransferase Catalyzed Methyl Esterification of Malonyl-Acyl Carrier Protein, an Essential Step in Biotin Synthesis," Journal of Biological Chemistry, Sep. 2012, 287(44):37010-37020.
Lin et al., "Biotin Sythesis Begins by Hijacking the Fatty Acid Synthetic Pathway," Nature Chem Biol., Sep. 2010, 6:682-688.
Uniprot Accession No. O32472, Jun. 11, 2014, 2 pages.
Uniprot Accession No. P0A6RO, May 14, 2014, 5 pages.
Uniprot Accession No. P0A8Z0, Jun. 11, 2014, 3 pages.
Uniprot Accession No. P0AGG2, Jun. 11, 2014, 3 pages.
Uniprot Accession No. P0AEK4, Jun. 11, 2014, 6 pages.
Uniprot Accession No. P0A6Q6, Jun. 11, 2014, 3 pages.
Uniprot Accession No. P0A953, Jun. 11, 2014, 4 pages.
Uniprot Accession No. P0AEK2, May 14, 2014, 4 pages.
Uniprot Accession No. P13001, Jun. 11, 2014, 4 pages.
Uniprot Accession No. Q5EU90, Feb. 19, 2014, 2 pages.
Uniprot Accession No. Q73Q47, May 14, 2014, 2 pages.
Uniprot Accession No. Q818X2, Jun. 11, 2014, 2 pages.
US Final Office Action in U.S. Appl. No. 14/092,115, mailed Oct. 27, 2015, 8 pages.
Westin et al., "The identification of a succinyl-CoA thioesterase suggests a novel pathway for succinate production in peroxisomes," J. Biol Chem, 2005, 280:38125-38132.
International Search Report and Written Opinion in Application No. PCT/US2014/049786, mailed Sep. 11, 2015, 17 pages.
Chinese Office Action in Chinese Application No. 201280040122.2, dated Jul. 17, 2015, 7 pages.
International Preliminary Report on Patentability and Written Opinion for PCT/US2013/072275, issued Jun. 2, 2015, 8 pages.
"Production of butadiene," China Synthetic Rubber Industry, Special issue of 1978, 21 pages (with partial English translation).
US Non-Final Office Action in U.S. Appl. No. 13/916,156, mailed Jul. 14, 2015, 35 pages.
Zhang et al., "Genes encoding acyl-CoA dehydrogenase (AcdH) homologues from Streptomyces coelicolor and Streptomyces avermitilis provide insights into the metabolism of small branched-chain fatty acids and macrolide antibiotic production," Microbiology, 1999, 145(9):2323-2334, 12 pages.
Zhuang et al., "Divergence of function in the Hotdog-fold enzyme superfamily: the bacterial thioesterase YciA," Biochemistry, 2008, 47(9):2789-2796, 8 pages.

\* cited by examiner

METHODS OF PRODUCING FOUR CARBON MOLECULES

RELATED APPLICATION

This application claims priority to U.S. provisional application No. 61/498,408 filed Jun. 17, 2011.

FIELD OF THE INVENTION

This application is related to a method for producing butadiene from one or more of several diverse feedstocks including bioderived feedstock, renewable feedstock, petrochemical feedstock and/or natural gas.

BACKGROUND OF THE INVENTION 1,3-Butadiene (hereinafter butadiene) is an important monomer for synthetic rubbers including styrene-butadiene rubber (SBR), plastics including polybutadiene (PB), acrylonitrile butadiene styrene (ABS), acrylonitrile butadiene (NBR), and as a raw material for adiponitrile for Nylon-6,6 other chemicals. Butadiene is typically produced as a byproduct in the steam cracking process and isolated from the cracker streams via extraction. On-purpose butadiene has been prepared among other methods by dehydrogenation of n-butane, dehydrogenation of n-butane, dehydration of n-butanol or butanediols. Industrially, butadiene has been synthesized using petrochemical-based feedstocks. The current commercial practices for producing on-purpose butadiene have several drawbacks including high cost of production and low yield processes. Currently, methods for the production of on-purpose butadiene rely on petro-chemical feedstocks and on energy intensive catalytic steps. In this regard, biotechnology offers an alternative approach in the form of biocatalysis. Biocatalysis is the use of natural catalysts, such as enzymes, to perform chemical transformations on organic compounds. Both enzymes that have been wholly or partially purified, and enzymes which are present in whole cells are useful catalysts in biocatalysis.

Accordingly, against this background, it is clear that there is a need for sustainable methods for producing intermediates, in particular butadiene, wherein the methods are biocatalysis based. Both bioderived feedstocks and petrochemical feedstocks are viable starting materials for the biocatalysis processes.

SUMMARY OF THE INVENTION

The inventors have determined that it is possible to generate enzymes which are able to catalyse the conversion of butenols to butadiene. Prior to the inventors' surprising discovery, it was not known that enzymes capable of introducing double bonds between carbon atoms in hydroxylated unsaturated four carbon molecules existed or could be generated.

The inventors' discovery is particularly surprising because the reaction catalysed by the enzymes of the invention is completely contrary to the typical reaction direction observed in nature. That is, the reaction is in the reverse direction to that which is observed in nature. In nature, double bonds between carbon atoms in a molecule, for example, in unsaturated fatty acids, tend be become saturated, for example, by an enzyme catalysed nucleophilic attack on one of the carbon atoms which is in the double bond. This is, in part, driven by the prevalent conditions of the intracellular milieu.

Thus, the invention provides enzymes which convert butenols into butadiene. This conversion can be performed by a single enzyme of the invention, or may be performed by two or more enzymes of the invention, acting sequentially (that is to say that, for example, a first enzyme acts on a four carbon molecule to produce a first butenol, and that first butenol is then acted upon by a second enzyme of the invention to produce butadiene). The invention also provides methods of producing butadiene from a unsaturated hydroxylated four carbon molecule, comprising at least one biocatalytic step. The reactions performed by the enzymes of the invention include dehydration (i.e. the removal of $H_2O$ from the molecule)

In some embodiments, the butenol is selected from the group consisting of 1-buten-3-ol, 1-buten-4b-ol, 2-buten-1-ol, 2-buten-3-ol or 2-buten-4-ol.

In some embodiments the butenol can be generated in situ as the enolate of the corresponding unsaturated ketone or aldehyde such as 1-butenal or 2-butenal or a 2-keto butene.

In some embodiments, a butenol is produced from four carbon molecules selected from a butanediol (1,4-butanediol, 1,3-butanediol, or 2,3-butanediol) or a butanol (1-butanol, or 2-butanol) or a butene (1-butene or 2-butene) by the action of an enzyme.

In some embodiments, the butenol is produced from a butene such as 1-butene or 2-butene.

The reactions performed by the enzymes of the invention will be dehydration (i.e. the removal of $H_2O$ from the molecule), oxidoeductase (i.e. the replacement of a hydrogen with a hydroxyl group), or dehydrogenation (i.e. the removal of hydrogen from the molecule). In the reactions catalysed by the enzymes of the invention, dehydrogenation results in a desaturation of the carbon backbone of the molecule. For the dehydration step the enzyme may be the same enzyme class as the enzyme class used for the dehydration of the butenol to butadiene or may be of another enzyme class.

In a separate invention, the invention provides an enzyme from the enzyme class 4.2.1.-.Enzymes in this class convert butanediols to butenol.

In some embodiments the butenol or butandiol can be derived from microbial fermentation processes based on biological or non-biological feedstocks. For instance, the butenol or butanediol can be derived from enzymatic or bioprocesses based on biological feedstocks such as glycerol, Synthesis Gas from biomass, sugars from food stuffs such as sucrose or glucose, or sugars from non-food stocks such as cellulosic or hemicellulosic derived sugars. Alternatively, the butenol or butandiol can be derived from bioprocesses based on non-biological feedstocks such as Synthesis Gas from coal, natural gas, combustion off-gases, and municipal waste or petrochemical derived feedstocks such as hydrocarbons. Further, the butenol or butanediol can be derived from non-enzymatic processes based on petrochemical feedstocks.

The reactions performed by the enzymes of the invention will be dehydration (i.e. the removal of $H_2O$ from the molecule).

In a separate invention, the invention provides an enzyme which converts butenes to butenols.

The butenol may be produced from four carbon molecules selected from the group consisting of a butene such as 1-butene or 2-butene. Further, the butenol may be selected from the group consisting of 1-buten-3-ol, 1-buten-4-ol, 2-buten-1-ol, 2-buten-3-ol or 2-buten-4-ol.

The reactions performed by the enzymes of the invention will be oxidoeductase (i.e. the replacement of a hydrogen with a hydroxyl group).

In another embodiment, the invention provides an enzyme or series of enzymes which converts butanols to butenols. A butenol is produced from four carbon molecules selected from the group consisting of a butanol such as 1-butanol or 2-butanol. Additionally, the butenol may be selected from the group consisting of 1-buten-3-ol, 1-buten-4-ol, 2-buten-1-ol, 2-buten-3-ol or 2-buten-4-ol.

In some embodiments, the butenol is produced directly from the butanol by action of a Cytochrome P450 type enzyme or other desaturase enzymes such as enzyme class 1.14.99.- or 1.3.1.- or directly from a butanediol by the action of a dehydratase In some embodiments, the butanol is formed via multiple enzymatic steps from oxidized intermediates such as 1-butanal, butyric acid, or butyric acid CoA prior to reaction with the desaturase enzyme resulting in a desaturaton of the carbon molecule. The unsaturated oxidized intermediates are thus reduced to a butenol.

In some embodiments the butanols and butanediols can be derived from enzymatic processes based on biological or non-biological feedstocks. For instance, the butanols and butanediols can be derived from enzymatic processes based on biological feedstocks such as glycerol, Synthesis Gas from biomass, sugars from food stuffs such as sucrose or glucose, or sugars from non-food stocks such as cellulosic or hemicellulosic derived sugars. Alternatively, the butanols and butanediols can be derived from enzymatic processes based on non-biological feedstocks such as Synthesis Gas from coal, natural gas, combustion off-gases, and municipal waste or petrochemical derived feedstocks such as hydrocarbons. Further, the butanols and butanediols can be derived from non-enzymatic processes based on petrochemical feedstocks.

The reactions performed by the enzymes of the invention will be dehydrogenation of butanols (i.e. the removal of $H_2$ from the molecule)or dehydration of butanediols by a dehydratase. In the reactions catalysed by the enzymes of the invention, dehydrogenation results in a desaturation of the carbon backbone of the molecule and dehydration results in the removal of a water molecule.

In another embodiment, the invention provides an enzyme or series of enzymes to produce butadiene from a non-hydroxylated four carbon molecule selected from the group n-butane, 1-butene, or 2-butene.

The reactions performed by the enzymes of the invention will be hydroxylation by a CytP450 enzyme.

The method of the invention can be used with any source of unsaturated hydroxylated four carbon molecule or its precursor, and therefore is suitable for integration into any known method for synthesising unsaturated hydroxylated four carbon molecules that can then be converted into butadiene. For example, the hydroxylated four carbon molecule may be generated by chemical synthesis or it may be produced biocatalytically. Methods of synthesising hydroxylated four carbon molecules are known in the art. Thus the invention provides a method of synthesising butadiene from substrates including: syngas, glycerol, $CO_2/H_2O$, $CO_2/H_2$, municipal solid waste (MSW), corn, wood pulp, lignocellulose, hemicellulose, macroalgae sugars or sugar, butane, 1-butene, 2-butene, n-butanol, iso-butanol, butyric acid,3-butanediol,2,3-butanediol, 1,4-butanediol, or butenals or 2-keto butene, comprising at least one enzyme-catalysed step, wherein one enzyme-catalysed step is the conversion of a butenol to butadiene.

The discovery of a biocatalytic method for the production of butadiene is particularly advantageous because it enables the conversion of four carbon molecules to butadiene without the extreme reaction conditions required for chemical catalysis of this reaction, which are highly energy intensive.

In one embodiment, the invention involves a method for producing butadiene by fermentation of a fermentable feedstock. The method includes steps of fermienting the fermentable feedstock in the presence of an organism to produce a fermentation broth comprising a C4-precursor, the precursor including butanol, butanediol, or both. The C4-precursor is fermented in the presence of the organism to convert at least a portion of the C4-precursor in the fermentation broth to produce butenol by a pathway comprising: (a) converting butanediol to butenol, or (b) converting butanol to butenol. The butenol is fermented in the presence of the organism to produce 1,3-butadiene in the fermentation broth. The 1,3-butadiene is then isolated from the broth.

In another embodiment, the invention involves a method for biocatalytically producing butadiene from feedstock. The feedstock is converted in the presence of a biocatalyst into at least a portion of a C4-precursor, the C4-precursor being butanol, butanediol, or both. The C4-precursor is then reacted with a biocatalyst to convert at least a portion of the C4-precursor in the fermentation broth to produce butenol by a pathway comprising: (a) converting butanediol to butenol, or (b) converting butanol to butenol. The butenol is converted to 1,3-butadiene with a second biocatalyst and then isolated.

In another embodiment, the invention involves a method for producing butadiene from fermentation of a petrochemical feedstock. The process includes obtaining butane or butene from the petrochemical feedstock. The butane or butene is then fermented in the presence of an organism to produce 1,3-butadiene in the fermentation broth, which is then isolated.

In another embodiment, the invention involves a method of biocatalytically producing butadiene from a petrochemical feedstock. Butane is obtained from the petrochemical feedstock. The butane is contacted with a first biocatalyst to produce butene. The butene is contacted with a second biocatalyst to produce 1,3-butadiene.

DETAILED DESCRIPTION OF THE INVENTION

Figure 1:
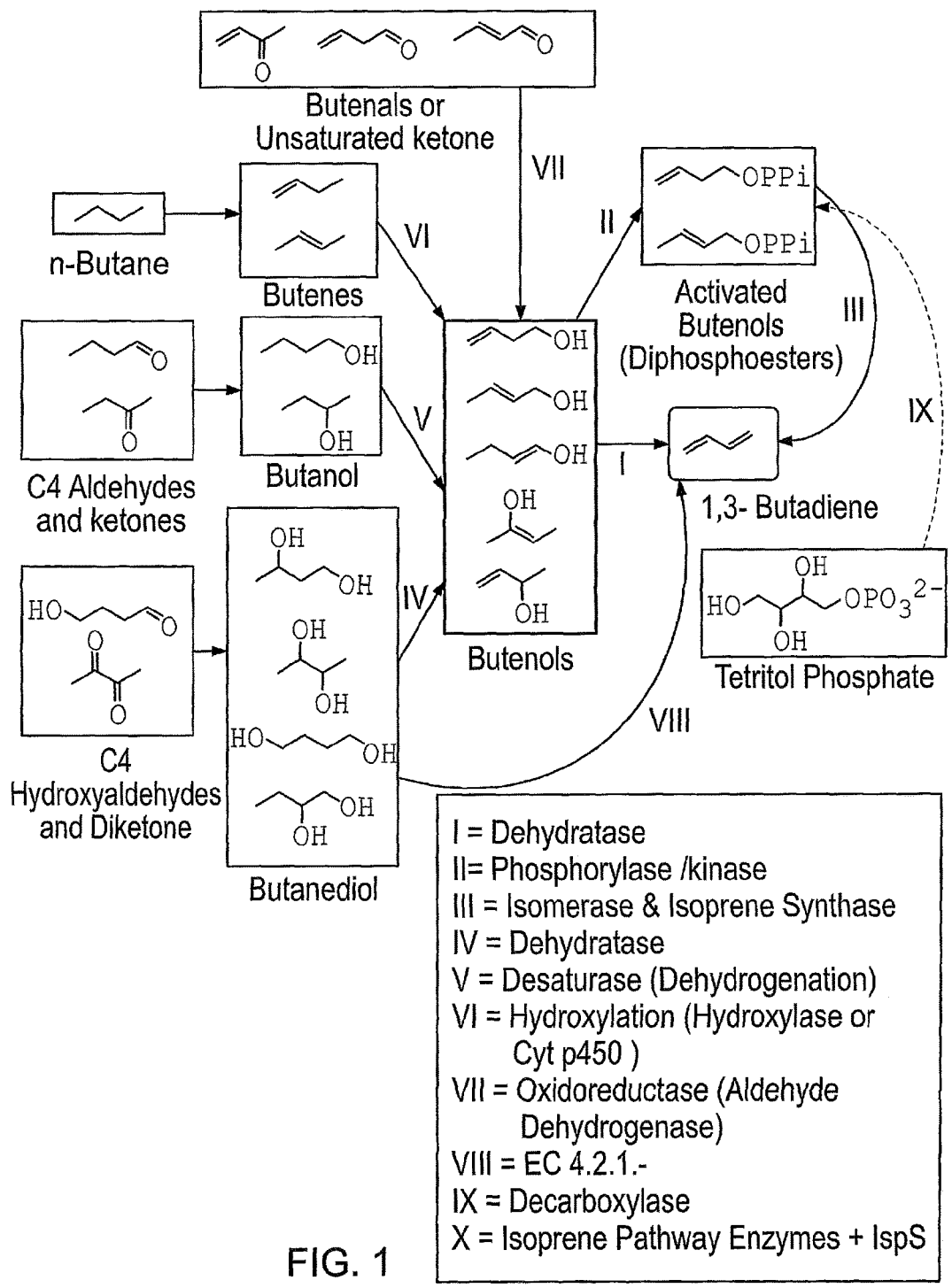
FIG. 1 is a chart showing pathways for enzymatic butadiene production according to the present invention.

The method of the invention uses one or more enzymes for a specific chemical reaction: the catalysis of the conversion of butenol to butadiene, the catalysis of the conversion of butanediol to butenol, the catalysis of the conversion of butene to butenol, the catalyst of conversion of butanol to butenol, the catalyst of conversion of unsaturated butyric acid to butadiene, or the catalysis of the conversion of nonhydroxylated four carbon molecules to butadiene. Catalysis by enzymes is highly specific, and thus it is common that a single enzyme will catalyse only a single reaction, and frequently will catalyse this reaction with only a low number of substrates. FIG. 1 illustrates several catalytic pathways for enzymatic production of butadiene according to the present invention.

The catalytic pathway for production of butadiene from fatty acid, glycerol, and sugars is illustrated in FIG. 1 Specifically, fatty acids, glycerols, and sugars may undergo glycolysis and/or fatty acid metabolism to produce acetyl-CoA. Acetyl-CoA may be converted to Acetoacetyl-CoA through E.C.2.3.1.9. The Acetoacetyl-CoA may then be converted to (S)-3-Hydroxybutanoyl-CoA by E.C.1.1.1.157. Alternatively, or in addition, 1,2-butanediol may be converted to 3-hydroxybutanal through EC 1.1.3.41 and then to (S)-3-Hydroxybutanoyl-CoA through EC 6.2.1.-. The conversion of (S)-3-Hydroxybutanoyl-CoA to Crotonyl-CoA may proceed via EC 4.3.1.17. The Crotonyl-CoA may be converted to vinylacetyl-CoA through EC 5.3.3.3, and conversion of vinylacetyl-CoA to 4-Hydroxybutyryl-CoA through EC 4.2.1.120. Further, 4-Hydroxybutyryl-CoA may be converted to 4-Hydroxybutanal through EC 3.2.1-abtT.

Figure 2:
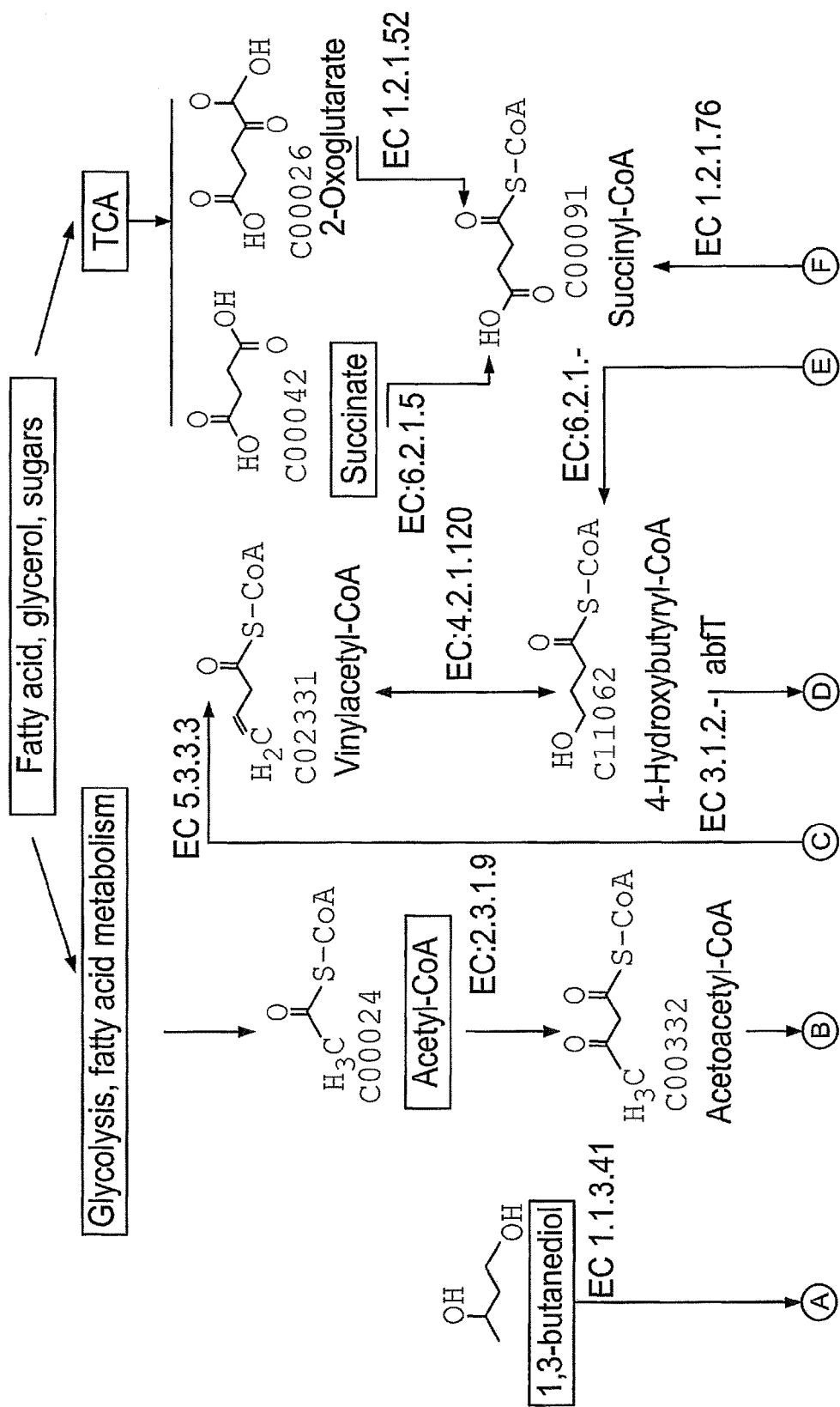
FIG. 2 is a chart showing detailed enzymatic pathways for butadiene production from fatty acid, glycerol, and sugar according to the present invention.
Figure 2:
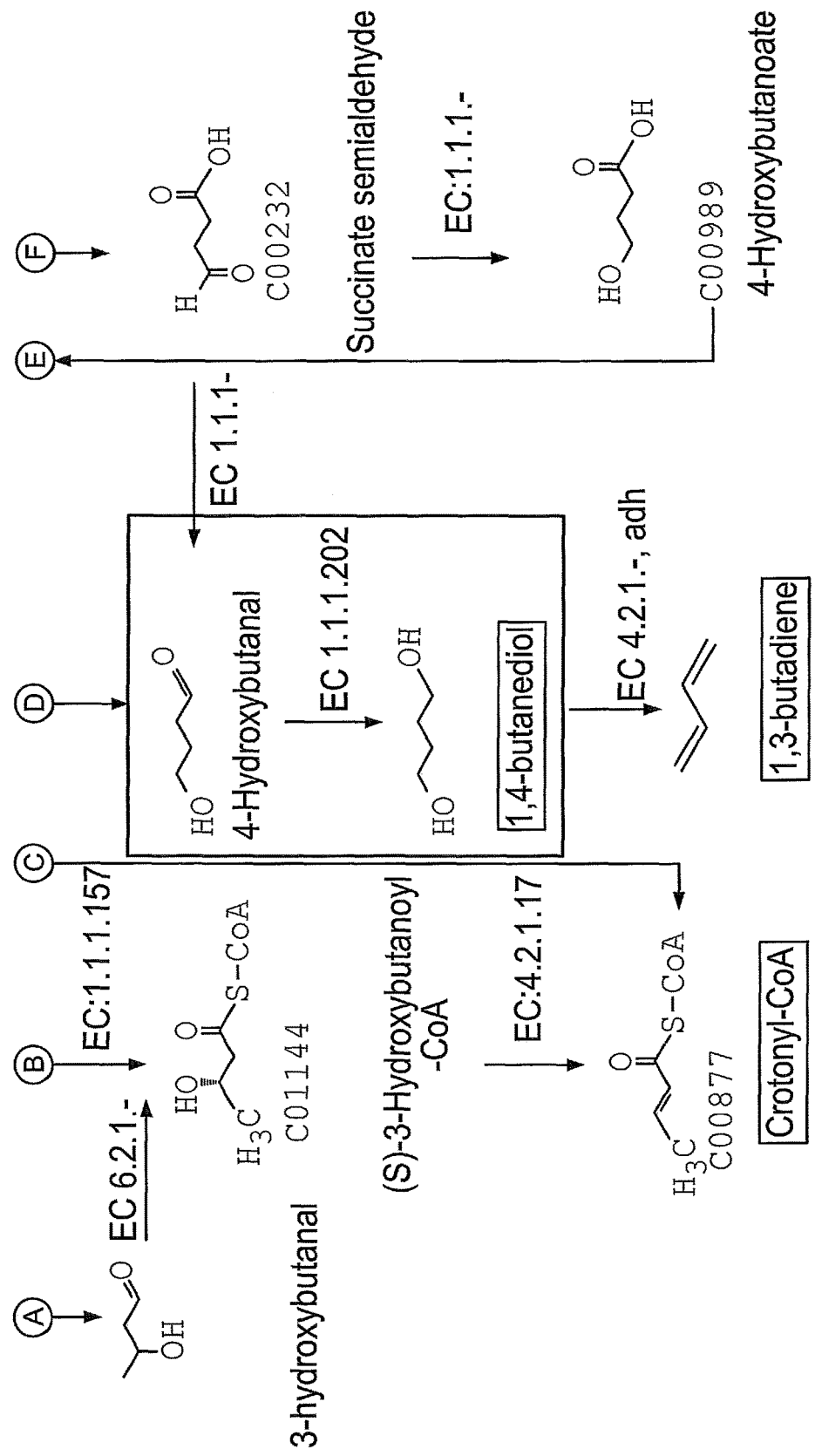

Alternatively, or in addition, fatty acid, glycerol, and/or sugar may be converted to Succinate and/or 2-Oxoglutarate through the tricarboxilic acid cycle (TCA cycle) as shown in FIG. 2. The succinate may be converted to via EC 6.2.1.5 and the 2-Oxoglutarate may be converted via EC 1.2.1.52 to succinyl-CoA. The succinyl-CoA may be converted via EC 1.2.1.76 to succinate semialdehyde, which may be converted to 4-hydroxybutanoate and optionally to 4-Hydroxybutanal through EC 1.1.1.-. Alternatively, or in addition, 4-hydroxybutanoate may be converted to 4-Hydroxybutyryl-CoA via EC 6.2.1.-, and then to 4-Hydroxybutanal through EC 3.2.1-abtT.

As further shown in FIG. 2, 4-Hydroxybutanal may be converted to 1,4-butanediol through EC 1.1.1.202. The 1,4-butanediol may then be converted to 1,3-butadiene through EC 4.2.1.-, adh. The 1,4-butanediol may then be isolated from the reaction medium. The reactions shown in FIG. 2 may be modified to include pathways shown in FIG. 1. For example 1,4-butanediol may be converted to butenol via a dehydratase enzyme alternatively or in addition to direct coversion to 1,4-butanediol as shown in FIG. 2. Further, any of the intermediate steps within the reaction chain shown may for the starting point for a commercially relevant production of 1,4-butadiene depending on the available feedstock.

Figure 3:
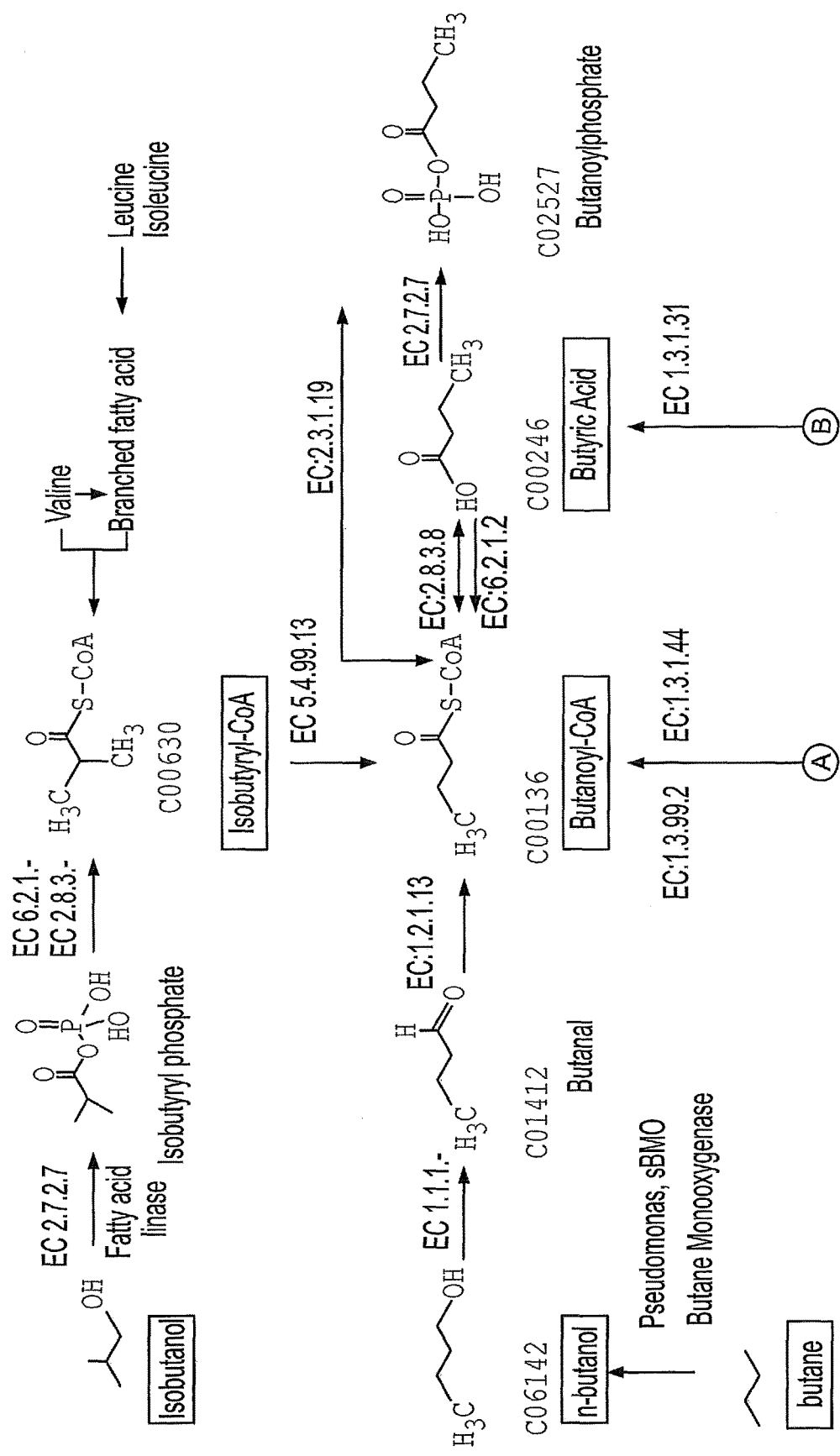
FIG. 3 is a chart showing showing detailed enzymatic pathways for butadiene production according to the present invention.
Figure 3:
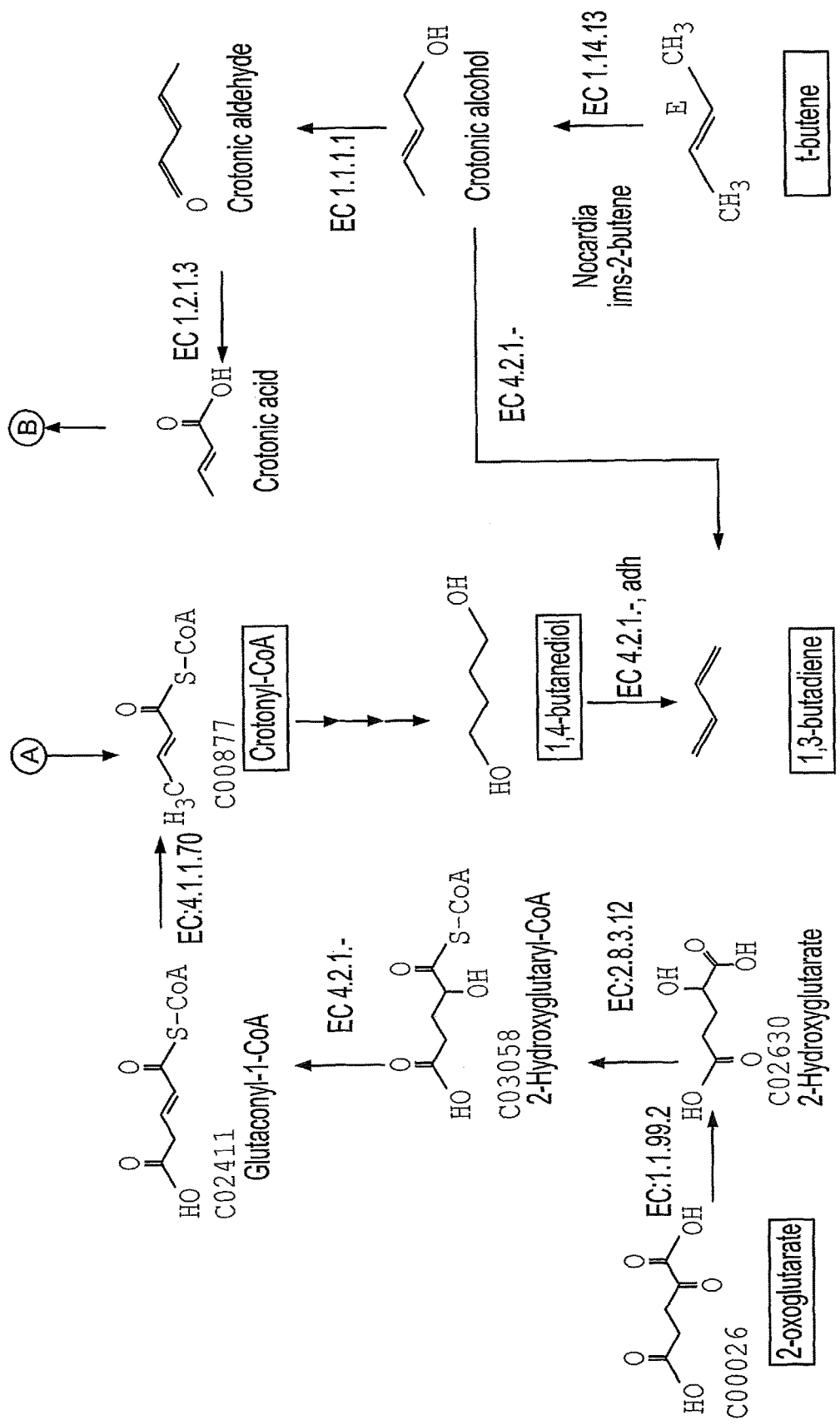

FIG. 3 illustrates additional pathways for conversion of various starting materials to butadiene. These starting materials include isobutanol, butane, 2-oxoglutarate, valine, leucine, isoleucine, butanoylphosphate, and/or t-butene. These pathways include the conversion of source materials from a petrochemical and/or natural gas feedstock such as butane. As with FIG. 2, the pathways shown in FIG. 3 may be integrated with other pathways described herein. For example, n-butanol may be converted to a butenol through the action of a desaturase enzyme as illustrated in FIG. 1, or may proceed via the pathway illustrated in FIG. 3 that results information of 1,4,-butanediol, which is then converted to 1,4-butadiene.

Suitable techniques for identifying, isolating and recombinantly manipulating enzymes are known in the art.

1.1. Enzyme Catalysed Conversions

The enzymes of the invention catalyse reactions in the conversion of hydroxylated four carbon molecules to butadiene.

The reactions catalysed by the enzymes of the invention include the dehydration of butenol such as 1-buten-3-ol, 1-buten-4-ol, 2-buten-1-ol,2-buten-3-ol or 2-buten-4-ol.to butadiene.

In an alternate reaction, the reactions catalysed by the enzymes of the invention include the dehydration of butanediol, such as 1,4-butanediol, 1,3-butanediol, and 2,3-butanediol, to butenols such as 1-buten-3-ol, 1-buten-4-ol, 2-buten-1-ol,2-buten-3-ol or 2-buten-4-ol. These enzymes may be the same enzymes capable of converting the butenols to butadiene or different enzymes or enzyme classes.

Thus, by combining these two steps of enzyme reactions it is possible to convert 1,4-butanediol, 1,3-butanediol, and 2,3-butanediol to butadiene. In this instance, the dehydratase enzyme may act first on the butanediol to produce butenol, which is then acted upon by the same or different dehydration enzyme to produce butadiene.

In an alternative reaction, a hydrolyase enzyme can be used to introduce a hydroxyl group into a non-hydroxylated four carbon molecule. Typically the substrate for this reaction will be 1-butene or 2-butene. Here, upon action of the oxidoreductase enzyme, a hydroxyl group is introduced either on the terminal carbon or the allylic carbon to produce a butenol. Thus, following reaction with this enzyme, 1-butene is converted to 1-buten-4-ol or 1-buten-3-ol and 2-butene is converted to 2-buten-1-ol (also known as crotonic alcohol). The 1-butene produced by the desaturation of butane will in turn be acted upon again by the enzyme to produced 1,3-butadiene. 1-butene-3-ol and 1-butene-4-ol may be dehydrated, using an enzyme as detailed above, to produce 1,3-butadiene.

Thus, by combining this oxidoeductase enzyme with the dehydration step of butenol enzyme it is possible to convert 1-butene and 2-butene to butadiene. In this instance, the hydrolase enzyme may act first on the butene to produce butenol, which is then acted upon by the dehydration enzyme to produce butadiene.

In an alternative reaction, a desaturase enzyme can be used to introduce a C=C bond into a saturated four carbon molecule. Typically the substrate for this reaction will be butan-1-ol, butan-2-ol, butane or 1-butene. Here, upon action of the desaturase enzyme, a C=C bond is introduced between the terminal carbon and the penultimate carbon (distal to the functional group present on the molecule in the case of butan-1-ol, butan-2-ol or 1-butene). Thus, following reaction with this enzyme, butan-1-ol, butan-2-ol, butane[1] or 1-butene is converted to 1-butene-4-ol, 1-butene-3-ol, 1-butene or 1,3-butadiene, respectively. The 1-butene produced by the desaturation of butane will in turn be acted upon again by the enzyme to produced 1,3-butadiene. 1-butene-3-ol and 1-butene-4-ol may be dehydrated, using an enzyme as detailed above, to produce 1,3-butadiene.

Thus by combining these two classes of enzymes it is possible to convert butan-1-ol and butan-2-ol to butadiene. In this instance, the dehydratase enzyme may act first on the butanol to produce 1-butene, which is then acted upon by the desaturase to produce butadiene. Alternatively, the desaturase may act first to produce 1-buten-3-ol or 1-buten-4-ol, which is then reacted to produce butadiene by the dehydratase enzyme.

In an alternate reaction, a desaturase enzyme can be used to introduce a double bond into a saturated four carbon carboxylic acid or aldehyde. Typically the substrate for this reaction will be butyric acid or butyraldehyde. Here, upon action of the desaturase enzyme, a C=C bond is introduced between the terminal carbon and the penultimate carbon (distal to the functional group present on the molecule in the case of butyric acid or butyraldehyde). Thus, following reaction with this enzyme, butyric acid or butyraldahyde is converted to 3-butene-carboxylic acid, 2-butene-carboxylic acid, 4-oxo-but-1-ene or 4-oxo-but-2-ene, respectively. The resultant unsaturated butyric acid or butyraldehyde will in turn be acted upon again by an enzyme or series of enzymes to produce the corresponding butenol. 2-butene-4-ol or 1-butene-4-ol may be dehydrated, using an dehydratase as detailed above, to produce 1,3-butadiene. The butyric acid and the butyraldehyde can be produced enzymatically from 1-butanol by action of an oxidase enzyme. Thus by combining these series of reactions 1-butanol can be converted to butadiene.

Enzymes suitable for use in the methods of the invention 1.1.1. Dehydratase Enzymes Dehydratases in EC 4.2.1.- can be used to catalyse a number of steps of reactions which convert butenols to butadiene and/or butanediols to butenols. See FIGS. 2-3.

Dehydratses according to the invention comprises enzymes which are capable of:
  a) dehydrating 1-butene-3-ol to produce butadiene;
  b) dehydrating 1-butene-4-ol to produce butadiene;
  c) dehydrating 2-butene-1-ol to produce butadiene.
  d) Dehydrating 2-buten-3-ol to produce butadiene
  e) Dehydrating 2-butene-4-ol to produce butadiene
  f) dehydrating 1,4-butanediol to produce 1-buten-4-ol;
  g) dehydrating 1,3-butanediol to produce 1-buten-3-ol, 1-buten-4-ol, or 2-buten-4-ol ; or
  h) dehydrating 2,3-butanediol to produce 1-buten-3-ol or 2-buten-3-ol 1.1.2. Desaturase Enzymes Desaturase enzymes of the invention introduce a double bond into n-butanol or iso-butanol at the saturated terminal carbon. Desaturases have been demonstrated in the prior art to introduce double bonds at specific positions in fatty acids. Furthermore, it is possible to modify the substrate- and regio-specificities of these enzymes. See Wang et al., "Alteration of Product Specificity of *Rhodobacter sphaeroides* Phytoene Desaturase by Direct Evolution," J. Biolog. Chem., Vol. 27, No. 44, Issue of November 2, pp. 41161-41164 (2001).

In particular, enzymes in the class EC 1.14.19.- have been found to be useful in performing the methods of the invention. Other enzymes that are capable of introducing double bonds into four carbon molecules include members of EC 1.14.99.-, such as 1.14.99.19/30/31/32/33. Enzymes in the class EC 1.3.1.35 are also capable of introducing double bonds. Accordingly, in some embodiments of the invention, the enzyme is in class EC 1.14.19.-, 1.14.99.-, for example 1.14.99.19, 1.14.99.30, 1.14.99.31, 1.14.99.32, 1.14.99.33, or 1.3.1.35.

1.1.3. Cytochrome P450 Enzymes

Aliphatic desaturation can also be catalysed by cytochrome P450 enzymes. Accordingly, in some embodiments of the invention the enzyme is a cytochrome P450. The CYP4 isozyme had been reported to catalyse terminal desaturation of valproic acid to form the 4-ene acid with high activity compared to CYP2. See Rettie et al., "CYP4 Isozyme Specificity and the Relationship between ω-Hydroxylation and Terminal Desaturation of Valproic Acid," Biochemistry, 34, 7889-7895 (1995).

1.1.4. Clavaminate Synthase 2

Like P450 enzymes, clavaminate synthase 2 can switch between hydroxylation and desaturation, depending on the substrate. 2-Oxogluterate—dependent non-heme iron enzymes of the clavaminate superfamily are thus also capable of introducing terminal double bonds in alkanes, alkenes, alkenols and alkenoic acids. In particular, clavaminate synthases of the class EC 1.14.11.22 are capable of converting hydroxylated four carbon molecules to butadiene. Accordingly, in some embodiments of the invention, the enzyme is in class EC 1.14.11.22.

1.1.5. Non-Naturally Occurring Enzymes

In some embodiments, the enzymes used to perform conversions in the method of the invention are non-naturally occurring. That is to say the DNA encoding them has been mutated from the wild type sequence in order to improve one or more of the enzyme's properties. Methods for mutagenesis of proteins are well known in the art. Random and/or combinatorial mutagenic approaches may alternatively or additionally be used for the creation of libraries of mutations, including approaches such as DNA shuffling, STEP and error prone PCR, molecular evolution and mutator strains. A non-limiting list of mutagenic changes includes deletions, insertions, substitutions, rearrangements, point mutations and suppressor mutations. The products of the mutagenic methods should then be screened for the desired activity. Thus in some embodiments the enzyme of the invention is derived from an enzyme as described in sections. By "derived" is meant that the enzyme contains one or more amino acid changes compared to the sequence of the wildtype enzyme, wherein the one or more changes includes deletions, insertions, substitutions, rearrangements, point mutations. The skilled person would understand that the EC classification system discussed in relation to the enzymes as described is highly specific, and depends on the specific substrates catalysed by an enzyme. Accordingly, an enzyme of the invention derived from one of the enzymes as described may be classified in a different EC category to wild type enzyme.

1.2. Biocatalyst Formatting

Whole cells that express one or more of the enzymes of the invention may be used as the biocatalyst. The whole cells that are used typically possess a number of properties: they may be easily genetically modified, are tolerant of the conditions used in the method of the invention, and grow to cells densities which are industrially useful.

In one alternative, the whole cell is a prokaryote. In another alternative it is a eukaryote. Typically single celled microorganisms are used.

The term prokaryotic cell includes gram positive and gram negative bacteria. Examples of gram negative bacteria which may be used with the methods of the invention include: *Escherichia coli, Rhodopseudomonas palustris*, sphingomonads, pseudomonads, and other bacteria belonging to *Salmonella, Burkholderia, Moraxella, Acaligenes, Psychrobacter, Thermotoga, Acinetobacteria, Rhodobacter, Azoarcus*, and *Rhodospirillum* genera. Examples of gram positive bacteria which may be used with the methods of the invention include: *streptococci, lactobacilli*, and other bacteria belonging to *Nocardia, Bacillus, Rhodococcus, Clostridium, Streptomyces*, and *Arthobacter* genera.

Eukaryotic host cells include those from yeast and other fungi. Examples of eukaryotic host cells which may be used with the methods of the invention include: *Yarrowia lipolytica, Candida* genera such as *Candida tropicalis, C. albicans, C. cloacae, C. guillermondii, C. intermedia, C. maltosa, C. parapsilosis, C. zeylenoides*, yeasts belonging to the *Rhodotorula, Rhizopus, Trichosporon*, and *Lipomyces* genera, and other fungi belonging to *Aspergillus, Exophiala, Mucor, Trichoderma, Cladosporium, Phanerochaete, Cladophialophora, Paecilomyces, Scedosporium*, and *Ophiostoma* genera.

1.3. Modification of Whole Cell Biocatalysts

The biocatalysts used in the methods of the invention may be unmodified whole cells of the species in which the enzyme naturally occurs. Typically, however, it is necessary to modify genetically the host cell. In one alternative, the genetic modification is the introduction of a nucleic acid into the genome of the cell. The nucleic acid introduced into the cell may comprise a nucleic acid sequence from another species or organism, for example a DNA sequence that is not present in the wildtype genome of the whole cell. In other instances, the introduced DNA sequence may be a further copy of a DNA sequence in the genome of the whole cell. In some alternatives, the genetic modification is the deletion of DNA sequence from the genome of the whole cell. In another alternative, the genetic modification is the modification of the genome of the cell.

1.4. Use of the Enzymes of the Invention in Whole Cells Engineered to Produce Hydroxylated Four Carbon Molecules Nucleic acids encoding the enzymes of the invention can be placed into known host cells which are capable of producing hydroxylated four carbon molecules, either as a product or an intermediate in the production of other compounds. By the extension or diversion of the biosynthetic pathways in these previously known host organisms engineered to produce hydroxylated four carbon molecules from renewable feedstocks such as carbohydrates and fatty acids, as well as from glycerol, syngas or photosynthesis. These pathways are extended or diverted to further convert the hydroxylated four carbon molecules or precursors thereof to butadiene.

1.5. Metabolic Engineering of Whole Cells

Metabolic engineering is the process of optimising the parameters in a whole cell in order to increase the ability of a cell to produce a compound. The whole cells used in the method of the present invention optionally have been engineered to optimise the output of the butadiene.

1.6. Growing Whole Cell Biocatalysts

In some embodiments of the invention whole cell biocatalysts are used which are growing (i.e. dividing) at the time the whole cells perform the conversions in the method of the invention. In these embodiments the cells are cultured under conditions which optimise the production of desired product (i.e. butadiene) or precursor (butonol or buitanediol). As used herein, the term culture is equivalent with fermentor and bioreactor.

1.7. Feedstocks for Process

In some embodiments the butadiene can be derived from enzymatic processes based on biological or non-biological feedstocks.

In some embodiments, the butadiene can be derived from enzymatic processes based on biological feedstocks such as glycerol, Synthesis Gas from biomass, sugars from food stuffs such as sucrose or glucose, or sugars from non-food stocks such as cellulosic or hemicellulosic derived sugars.

In some embodiments the butadiene can be derived from enzymatic processes based on non-biological feedstocks such as Synthesis Gas from coal, natural gas, combustion off-gases, and municipal waste or petrochemical derived feedstocks such as hydrocarbons.

In some embodiments, the butadiene can be derived from non-enzymatic processes based on petrochemical feedstocks.

1.8. Compositions of the Invention

The invention also provides compositions comprising an enzyme of the invention and a four carbon molecule. The invention further provides compositions comprising an enzyme of the invention and 1,3-butadiene.

The invention claimed is:

1. A method for producing 1,3-butadiene comprising:
fermenting a fermentable feedstock in the presence of a genetically modified microorganism under conditions to produce 1,3-butadiene, wherein said genetically modified microorganism comprises heterologous nucleic acids encoding a dehydratase enzyme classified under EC 4.2.1.- and a desaturase enzyme selected from the group consisting of cytochrome P450 enzymes, clavaminate synthase 2 enzymes, and enzymes classified under EC 1.14.19-, EC 1.14.99-, EC 1.3.1-; and isolating said 1,3-butadiene.

2. The method of claim 1, wherein said fermentable feedstock is a non-biologically derived feedstock.

3. The method of claim 2, wherein said non-biologically derived feedstock is synthesis gas from coal, natural gas, combustion off-gases, municipal waste, petrochemical, or combinations thereof.

4. The method of claim 2, wherein said non-biologically derived feedstock is a petrochemical.

5. A method of producing 1,3-butadiene comprising:
contacting butenol with a dehydratase enzyme classified under EC 4.2.1- to dehydrate said butenol to produce 1,3-butadiene, wherein said butenol is selected from the group consisting of 1-buten-3-ol, 1-buten-4-ol, 2-buten-1-ol, 2-buten-2-ol, 1-buten-1-ol, and 1-buten-2-ol.

6. The method of claim 5, wherein said butenol is 1-buten-3-ol.

7. The method of claim 5, further comprising:
contacting butanol with a desaturase enzyme to produce said butenol, wherein said desaturase enzyme is selected from the group consisting of, cytochrome P450 enzymes, clavaminate synthase 2 enzymes, and enzymes classified under EC 1.14.19-, EC 1.14.99-, EC 1.3.1-.

8. The method of claim 7, wherein said desaturase is classified under EC 1.14.19-, EC 1.14.99-, or EC 1.3.1-.

9. The method of claim 7, wherein said desaturase is a cytochrome P450 enzyme.

10. The method of claim 9, wherein said cytochrome P450 enzyme is CYP4.

11. The method of claim 7, wherein said desaturase is a clavaminate synthase 2 enzyme.

12. The method of claim 11, wherein said clavaminate synthase 2 enzyme is classified under EC 1.14.11.22.

* * * * *

UNITED STATES PATENT AND TRADEMARK OFFICE
CERTIFICATE OF CORRECTION

PATENT NO. : 9,663,801 B2  
APPLICATION NO. : 13/524973  
DATED : May 30, 2017  
INVENTOR(S) : Paul S. Pearlman Page 1 of 1

It is certified that error appears in the above-identified patent and that said Letters Patent is hereby corrected as shown below:

In the Claims

Column 10, Line 22, add -- or -- between EC 1.14.99-, and EC 1.3.1-;

Column 10, Line 46, add -- or -- between EC 1.14.99-, and EC 1.3.1-.

Signed and Sealed this
Third Day of October, 2017

Joseph Matal
*Performing the Functions and Duties of the*
*Under Secretary of Commerce for Intellectual Property and*
*Director of the United States Patent and Trademark Office*